United States Patent [19]

Turk et al.

[11] 4,118,558

[45] Oct. 3, 1978

[54] 2-ARYL-6-ARYLIDENE-1-(SUBSTITUTED AMINOALKOXY)-1-CYCLOHEXENES

[75] Inventors: Chester F. Turk, Kendall Park; John Krapcho, Somerset, both of N.J.

[73] Assignee: E. R. Squibb & Sons, Inc., Princeton, N.J.

[21] Appl. No.: 872,122

[22] Filed: Jan. 25, 1978

Related U.S. Application Data

[63] Continuation-in-part of Ser. No. 771,867, Feb. 25, 1977, Pat. No. 4,085,142.

[51] Int. Cl.² ............................................. C09B 23/00
[52] U.S. Cl. ................................ 542/429; 260/590 C; 424/249; 424/250; 424/267; 424/274
[58] Field of Search ........................................ 542/429

[56] References Cited

U.S. PATENT DOCUMENTS

| 3,560,554 | 2/1971 | Budai et al. ........................ 260/471 |
| 4,053,514 | 10/1977 | Krapcho et al. .................. 542/429 X |

OTHER PUBLICATIONS

Bachmann et al., "Journal American Chemical Society", vol. 72, pp. 3388-3392 (1950).

*Primary Examiner*—Robert V. Hines
*Attorney, Agent, or Firm*—Lawrence S. Levinson; Merle J. Smith; Donald J. Barrack

[57] ABSTRACT

Compounds having the formula

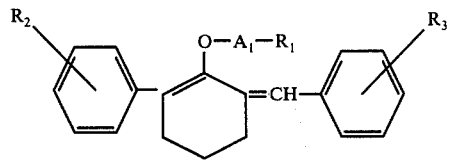

and pharmaceutically acceptable salts thereof, wherein $R_1$ is 1-pyrrolidinyl, 1-piperidinyl, 4-morpholinyl, 1-piperazinyl, or 4-alkyl-1-piperazinyl, $R_2$ and $R_3$ are hydrogen, chloro, fluoro, alkyl, alkoxy or trifluoromethyl, and $A_1$ is alkylene have antiinflammatory activity.

9 Claims, No Drawings

2-ARYL-6-ARYLIDENE-1-(SUBSTITUTED AMINOALKOXY)-1-CYCLOHEXENES

This is a continuation-in-part of copending U.S. patent application Ser. No. 771,867, filed Feb. 25, 1977 and now U.S. Pat. No. 4,085,142.

BACKGROUND OF THE INVENTION

Bachmann et al., *Jour. Amer. Chem. Soc.*, 72:3388 (1950) discloses 2-phenyl-6-benzylidenecyclohexanone, which is an intermediate in the preparation of some of the compounds of this invention. The reference also discloses 6-benzylidene-2-dimethylaminomethyl-2-phenylcyclohexanone. No utility is disclosed by the reference for any of the compounds.

BRIEF DESCRIPTION OF THE INVENTION

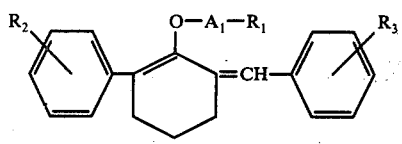

and the pharmaceutically acceptable salts thereof, have anti-inflammatory activity. In formula I, and throughout the specification, the symbols are as defined below.

$R_1$ is alkylamino, dialkylamino, 1-pyrrolidinyl, 1-piperidinyl, 4-morpholinyl, 1-piperazinyl or 4-alkyl-1-piperazinyl;

$R_2$ and $R_3$ are the same or different and are hydrogen, chloro, fluoro, alkyl, alkoxy or trifluoromethyl; and $A_1$ is alkylene (straight or branched chain) having 2 to 5 carbon atoms.

The term "alkyl", as used throughout the specification, whether by itself or as part of a larger group, refers to groups having 1 to 8 carbon atoms.

The term "alkoxy", as used throughout the specification, whether by itself or as part of a larger group, refers to groups having the formula alkyl-O-, wherein alkyl is as defined above.

DETAILED DESCRIPTION OF THE INVENTION

The compounds of this invention can be prepared using as starting materials a 2-arylcyclohexanone having the formula

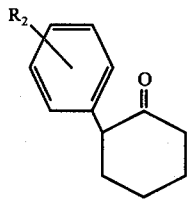

and a benzaldehyde having the formula

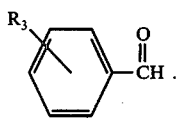

Reaction of a 2-arylcyclohexanone of formula II and a benzaldehyde of formula III yields a 2-aryl-6-arylidenecyclohexanone having the formula

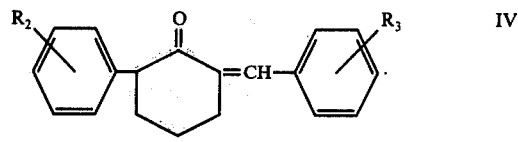

The reaction can be run in an organic solvent, preferably an alcohol having 1 to 4 carbon atoms, and is carried out in the presence of a base. The temperature at which the reaction is run is not critical, and the reaction can be conveniently carried out at room temperature.

The 2-aryl-6-arylidenecyclohexanones of formula IV exist as tautomeric mixtures; the keto and enol forms are as shown below:

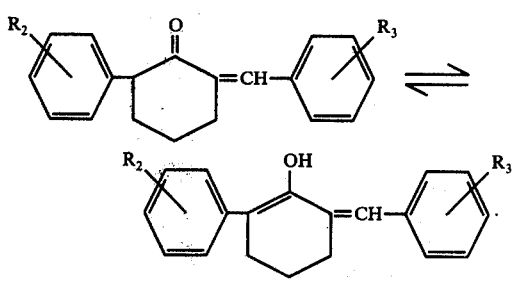

When a 2-aryl-6-arylidenecyclohexanone of formula IV is reacted with reagents such as butyl lithium, sodium hydride, sodium amide, potassium-t-butoxide, etc., the equilibrium reaction pictured above is driven towards the enol form, and yields a compound having the formula

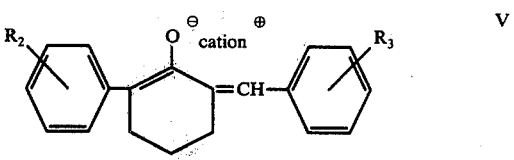

The reaction can be run in an organic solvent, e.g., a hydrocarbon solvent (or mixture of solvents).

An intermediate of formula V can be alkylated using procedures well known in the art to yield the corresponding product of formula I. The alkylating agent can have the formula $$R_1\text{—}A_1\text{—}X,\qquad\text{VI}$$

wherein X is chlorine or bromine.

Alternatively, the compounds of formula I can be prepared by first reacting a compound of formula V with a dihalo compound having the formula $$X\text{—}A_1\text{—}X\qquad\text{VII}$$

to yield an intermediate having the formula

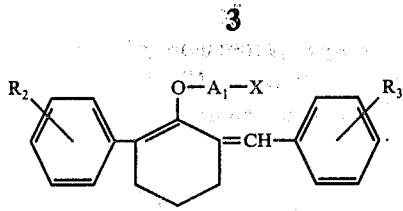

An intermediate of formula VIII can be reacted with an amine ($R_1H$) to yield the corresponding product of formula I. This procedure is particularly useful in preparing compounds of formula I wherein $A_1$ is alkylene of 4 to 5 carbon atoms, and also in preparing compounds of formula I wherein $R_1$ is alkylamino.

The compounds of formula I form acid addition salts with inorganic and organic acids. These acid addition salts can be used for isolating the intermediates and products described above from reaction mixtures by forming the salt in a medium in which it is insoluble. The free base may then be obtained by neutralization, and any other salt may then be formed by reaction of the free base with the appropriate acid. Exemplary salts are the hydrohalides (especially the hydrochloride and hydrobromide which are preferred), sulfate, nitrate, phosphate, borate, acetate, pamoate, tartrate, citrate, maleate, benzoate, methanesulfonate, toluenesulfonate and the like.

The compounds of formula I, and the pharmaceutically acceptable salts thereof, are useful for the treatment of inflammation in mammalian species, e.g., rats, dogs, cats, monkeys, etc. Joint tenderness and stiffness (in conditions such as rheumatoid arthritis) are relieved by the above-described compounds.

The compounds of this invention, and the pharmaceutically acceptable salts thereof, can be formulated for use as antiinflammatory agents according to accepted pharmaceutical practice in oral dosage forms such as tablets, capsules, elixirs or powders, or in injectable form in a sterile aqueous vehicle prepared according to conventional pharmaceutical practice. The compounds of this invention may be administered in amounts of 100 milligrams per 70 kilograms of animal body weight per day to 2 grams per 70 kilograms of animal body weight per day, preferably 100 milligrams per 70 kilograms of animal body weight per day to 1 gram per 70 kilograms of animal body weight per day.

Compounds of formula I wherein $A_1$ is —$(CH_2)_2$— or —$(CH_2)_3$— are preferred.

The following examples are specific embodiments of this invention.

EXAMPLE 1

N,N-Dimethyl-2-[[2-phenyl-6-(phenylmethylene)-1-cyclohexen-1-yl]oxy]ethanamine, hydrochloride (1:1)

(A) 2-Phenyl-6-(phenylmethylene)cyclohexanone

A solution of 60,0 g of 2-phenylcyclohexanone in 400 ml of ethanol is stirred and treated with 160 ml of 15% aqueous sodium hydroxide and 53.0 g of benzaldehyde. The resulting solution is stirred at room temperature and the product begins to separate from solution as an oil after 30 minutes. The mixture is seeded with crystalline material and allowed to stand overnight at room temperature. The resulting slurry is poured onto 1.5 liters of ice-water, allowed to stand at room temperature for 2 hours, filtered and washed with cold water. This material weights 81.2 g, melting point 75°–78° C. After crystallization from 200 ml of isopropanol, the product weighs 62.1 g; melting point 85°–87° C. A small sample, recrystallized from ethanol, melts at 86°–88° C.

(B) N,N-Dimethyl-2-[[2-phenyl-6-(phenylmethylene)-1-cyclohexen-1-yl]oxy]ethanamine, hydrochloride (1:1)

A stirred solution of 10 g of 2-phenyl-6-(phenylmethylene)cyclohexanone in 70 ml of dimethylformamide is treated portionwise with 2.0 g of 50% sodium hydride (oil dispersion). A red color develops, accompanied by effervescence and a temperature rise (latter kept at less than 40° C.). After warming to 60° C. and cooling to 25° C., the mixture is treated with 30 ml of a 1.98 N toluene solution of 2-dimethylaminoethyl chloride, followed by 0.4 g of sodium iodide, and heated at 100°–105° C. for 3 hours.

After standing for about 16 hours at room temperature, the mixture is poured into 500 ml of cold water and the precipitated oil extracted with ether (five 100 ml portions). The combined ether layers are extracted with a cold solution of 6 ml of concentrated hydrochloric acid in 100 ml of water, followed by 25 ml of water. The combined aqueous phases are layered over with 100 ml of ether, stirred, basified with 12 g of potassium carbonate, the layers separated, the aqueous phase extracted with additional ether (four 100 ml portions), the combined ether layers dried, and the solvents evaporated to give 8.9 g of an oil. The base is dissolved in 100 ml of dichloromethane, treated with 4.3 ml of 6.1 N alcoholic hydrogen chloride, and the solvents removed on a rotary evaporator to give a glass-like residue which is dissolved in 50 ml of warm acetonitrile. On seeding and rubbing, the crystalline hydrochloride salt gradually separates; weight after cooling about 16 hours, 5.8 g; melting point 162°–163° C. Following recrystallization from 20 ml of acetonitrile, the product weights 4.8 g; melting point 164°–166° C.

EXAMPLE 2

N,N-Dimethyl-3-[[2-phenyl-6-(phenylmethylene)-1-cyclohexen-1-yl]oxy]propanamine, hydrochloride (1:1)

A stirred solution of 10 g of 2-phenyl-6-(phenylmethylene)cyclohexanone (see Example 1A) in 450 ml of toluene is treated fairly rapidly through an addition funnel with 20 ml of 2.1 N butyl lithium in hexane; the temperature rises steadily to 38° C. When the temperature begins to drop, the solution is warmed to 60° C., cooled to 25° C., treated with 30 ml of 2N 3-dimethylaminopropyl chloride in toluene, followed by 0.4 g of sodium iodide, and refluxed for 6 hours.

After standing for about 16 hours, the mixture is stirred for 30 minutes with 50 ml of water, the layers separated, and the aqueous phase extracted with a cold solution of 8 ml of concentrated hydrochloric acid in 125 ml of water. A viscous layer at the interface is separated with the lower aqueous phase. The organic layer is next extracted with 50 ml of water and the combined aqueous layers and the above middle layer are washed with ether. At this point two clear layers are obtained.

The aqueous phase is separated, layered over with ether, stirred, basified with 16 g of potassium carbonate, the layers separated, the aqueous phase extracted with additional ether (three portions), the combined ether layers dried, and the solvents evaporated to give 10.3 g of an oil. After standing for about 16 hours at room temperature to allow any unchanged halide to quaternize, the base is redissolved in ether, filtered, and the solvent evaporated to give 8.4 g of an oil.

The base in dichloromethane is treated with 1 equivalent of alcoholic hydrogen chloride and the solvents removed on a rotary evaporator to give a viscous residue which is dissolved in 50 ml of warm acetonitrile and diluted with 100 ml of ether. On seeding and rubbing, the crystalline hydrochloride salt separates; weight after cooling for about 16 hours, 5.8 g; melting point 154°–156° C. Following crystallization from methanol-ether, the product weighs 4.0 g; melting point 154°–156° C.

EXAMPLE 3

3-[[6-[(4-Chlorophenyl)methylene]-2-phenyl-1-cyclohexen-1-yl]oxy]-N,N-dimethylpropanamine, hydrochloride (1:1)

(A) 2-[(4-Chlorophenyl)methylene]-6-phenylcyclohexanone

Fifty grams of 2-phenylcyclohexanone, 54.0 g of 4-chlorobenzaldehyde and a solution of 20 g of sodium hydroxide in 125 ml of water are reacted in 300 ml of ethanol according to the procedure described in part A of Example 1 to yield 81.2 g of material, melting point 103°–109° C. After crystallization from 100 ml of acetonitrile, the crystalline product weighs 61.6 g, melting point 118°–120° C.

(B) 3-[[6-[(4-Chlorophenyl)methylene]-2-phenyl-1-cyclohexen-1-yl]oxy]-N,N-dimethylpropanamine, hydrochloride (1:1)

Interaction of 20.8 g of 2-[(4-chlorophenyl)methylene]-6-phenylcyclohexanone with 3.4 g of 50% sodium hydride (oil dispersion) in 100 ml of dimethylformamide, followed by 50 ml of 2.15 N toluene solution of 3-dimethylaminopropyl chloride and 0.5 g of sodium iodide according to the procedure described in part B of Example 1 yields 21.6 g of a syrup. The syrup is dissolved in 700 ml of ether and treated with a solution of 10.5 ml of 5.5 N ethanolic hydrogen chloride in 100 ml of ether. The solid which separates from solution is allowed to stand for about 4 hours to give 22.9 g of material, melting point 150°–157° C. (sintering at 140° C.). This material is dissolved in 60 ml methanol at room temperature and the solution is diluted to 600 ml with ether to give 17.7 g of the title compound, melting point 171°–173° C.

EXAMPLE 4

N-Ethyl-4-[[2-phenyl-6-(phenylmethylene)-1-cyclohexen-1-yl]oxy]butanamine (A) 1-Bromo-4-[[2-phenyl-6-(phenylmethylene)-1-cyclohexen-1-yl]oxy]butane A stirred solution of 2-phenyl-6-(phenylmethylene)-cyclohexanone (see Example 1A) in dimethylformamide is treated portionwise with 50% sodium hydride (oil dispersion), and then with 1,4-dibromobutane to yield the title compound.

(B) N-Ethyl-4-[[2-phenyl-6-(phenylmethylene)-1-cyclohexen-1-yl]oxy]butanamine

1-Bromo-4-[[2-phenyl-6-(phenylmethylene)-1-cyclohexen-1-yl]oxy]butane is dissolved in toluene, treated with two equivalents of ethyl amine and allowed to stand at room temperature for 1 day, and washed with potassium carbonate solution. Evaporation of the toluene yields the title compound.

EXAMPLE 5–15

Following the procedure of Example 1, but substituting the compound listed in column I for 2-phenylcyclohexanone, the compound listed in column II for benzaldehyde, and the compound listed in column III for 2-dimethylaminoethyl chloride, yields the hydrochloride of the compound listed in column IV.

| Column I | Column II | Column III | Column IV |
| --- | --- | --- | --- |
| 2-(2-chlorophenyl)cyclohexanone | benzaldehyde | 3-dimethylaminopropyl chloride | 3-[[2-(2-chlorophenyl)-6-(phenylmethylene)-1-cyclohexen-1-yl]oxy]-N,N-dimethylpropanamine |
| 2-(2-fluorophenyl)cyclohexanone | 2-fluorobenzaldehyde | 1-(2-bromoethyl)piperazine | 2-(2-fluorophenyl)-6-[(2-fluorophenyl)methylene]-1-[2-(1-piperazinyl)ethoxy]-1-cyclohexene |
| 2-(4-methylphenyl)cyclohexanone | benzaldehyde | 1-(3-bromopropyl)piperidine | 2-(4-methylphenyl)-6-(phenylmethylene)-1-[3-(1-piperidinyl)propoxy]-1-cyclohexene |
| 2-phenylcyclohexanone | 4-methylbenzaldehyde | 1-(3-bromopropyl)-4-methylpiperazine | 6-[(4-methylphenyl)methylene]-1-[3-(4-methyl-1-piperazinyl)propoxy]-2-phenyl-1-cyclohexene |
| 2-(4-methoxyphenyl)cyclohexanone | 4-methoxybenzaldehyde | 1-(2-bromoethyl)pyrrolidine | 2-(4-methoxyphenyl)-6-[(4-methoxyphenyl)methylene]-1-[2-(1-pyrrolidinyl)ethoxy]-1-cyclohexene |
| 2-(3-trifluoromethylphenyl)cyclohexanone | 3-trifluoromethylbenzaldehyde | 4-(3-bromopropyl)morpholine | 1-[3-(4-morpholinyl)propoxy]-2-(3-trifluoromethylphenyl)-6-[(3-trifluoromethylphenyl)methylene]-1-cyclohexene |
| 2-(2-chlorophenyl)cyclohexanone | 2-chlorobenzaldehyde | 2-dioctylaminoethyl chloride | 2-[[2-(2-chlorophenyl)-6-[(2-chlorophenyl)methylene]-1-cyclohexen-1-yl]oxy]-N,N-dioctylethanamine |
| 2-phenylcyclohexanone | 2-fluorobenzaldehyde | 3-diisopropylaminopropyl chloride | 3-[[6-[(2-fluorophenyl)methylene]-2-phenyl-1-cyclohexen-1-yl]oxy]-N,N-diiso- |

| Column I | Column II | Column III | Column IV |
|---|---|---|---|
| 2-phenylcyclohexanone | 4-methylbenzaldehyde | 2-dimethylamino-2-methylethyl chloride | propylpropanamine N,N-dimethyl-1-methyl-2-[[6-[(4-methylphenyl)-methylene]-2-phenyl-1-cyclohexen-1-yl]oxy]-ethanamine |
| 2-phenylcyclohexanone | 4-methoxybenzaldehyde | 3-dimethylaminopropyl chloride | 3-[[6-[(4-methoxy-phenyl)methylene]-2-phenyl-1-cyclohexen-1-yl]oxy]-N,N-dimethyl-propanamine |
| 2-(3-trifluoromethylphenyl)-cyclohexanone | 3-trifluoro-methylbenzaldehyde | 2-dioctylaminoethyl chloride | N,N-dioctyl-2-[[2-[3-tri-fluoromethylphenyl]-6-[(3-trifluoromethyl-phenyl)methylene]-1- |
| cyclohexen-1-yl]oxy]- | | | ethanamine |

EXAMPLE 16

4-[2-[[2-Phenyl-6-(phenylmethylene)-1-cyclohexen-1-yl]oxy]ethyl]morpholine, and salts thereof Interaction of 15 g of 2-phenyl-6-(phenylmethylene)-cyclohexanone (see Example 1A), 3.0 g of 50% sodium hydride (oil dispersion), 45 ml of a 2N toluene solution of 2-(4-morpholinyl)ethyl chloride and 0.6 g of sodium iodide in 105 ml of dimethylformamide following the procedure described in Example 1B yields 19.3 g of the crude hydrochloride salt which separates during the work-up while shaking with dilute hydrochloric acid. Crystallization from 150 ml of warm isopropanol—600 ml of ether yields 13.1 g of the hydrochloride salt of the title compound, melting point 158°–160° C.

The above salt is converted into the corresponding free base using conventional techniques (5 g of potassium carbonate; dichloromethane extractions). The free base has a melting point of 67°–69° C.

A solution of the above free base in 400 ml of ether is treated with a solution of 3.0 g of 97% methanesulfonic acid in 50 ml of ether to precipitate the methanesulfonate salt of the title compound as a gum. The gum solidifies on rubbing and then cooling for about 16 hours. Crystallization from 50 ml of acetonitrile yields 11.2 g of the methanesulfonate salt, melting point 162°–164° C., sintering at 159° C.

What is claimed is:

1. A compound having the formula

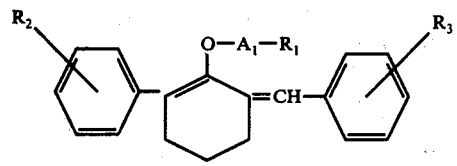

or a pharmaceutically acceptable salt thereof, wherein $R_1$ is 1-pyrrolidinyl, 1-piperidinyl, 4-morpholinyl, 1-piperazinyl, 4-alkyl-1-piperazinyl;

$R_2$ and $R_3$ are the same or different and are hydrogen, chloro, fluoro, alkyl, alkoxy or trifluoromethyl; and $A_1$ is alkylene having 2 to 5 carbon atoms; wherein the terms alkyl and alkoxy refer to groups having 1 to 8 carbon atoms.

2. A compound in accordance with claim 1 wherein $R_2$ and $R_3$ are hydrogen.

3. A compound in accordance with claim 1 wherein $A_1$ is —(CH$_2$)$_2$— or —(CH$_2$)$_3$—.

4. A compound in accordance with claim 1 wherein $R_1$ is 1-pyrrolidinyl.

5. A compound in accordance with claim 1 wherein $R_1$ is 1-piperidinyl.

6. A compound in accordance with claim 1 wherein $R_1$ is 4-morpholinyl.

7. A compound in accordance with claim 1 wherein $R_1$ is 1-piperazinyl.

8. A compound in accordance with claim 1 wherein $R_1$ is 4-alkyl-1-piperazinyl.

9. The compound in accordance with claim 6, 4-[2-[[2-phenyl-6-(phenylmethylene)-1-cyclohexen-1-yl]ethyl]morpholine.

* * * * *